United States Patent
Pelle

[11] Patent Number: 5,855,897
[45] Date of Patent: Jan. 5, 1999

[54] TOPICAL COMPOSITION AND METHOD FOR ENHANCING LIPID BARRIER SYNTHESIS

[75] Inventor: Edward Pelle, Valley Stream, N.Y.

[73] Assignee: E-L Management Corp., New York, N.Y.

[21] Appl. No.: 712,988

[22] Filed: Sep. 13, 1996

[51] Int. Cl.$^6$ ................................................ A61K 9/08
[52] U.S. Cl. ........................ 424/401; 424/59; 424/63; 424/400; 514/174; 514/461
[58] Field of Search .................... 424/400, 401, 424/59, 63; 514/169–171, 172, 174, 182, 469, 461

[56] References Cited

U.S. PATENT DOCUMENTS 4,793,990 12/1988 Grollier et al. .......................... 424/59

FOREIGN PATENT DOCUMENTS 1770352 10/1992 Russian Federation .

OTHER PUBLICATIONS

Miller et al., Kahweol and Cafestol: Inhibitors of Hamster Buccal Pouch Carcinogenesis, Nutrition and Cancer 15: 41–46, 1991.

Hugget et al, Chemoprotective Effects of Coffee and its Components Cafestol and Kahweol: Effects Xenobiotic Metabolizing Enzymes, Colloq. Sci. Int. Cafe (C.R.) 16(1): 65–72, 1995.

Urgert et al., Effects of Cafestol and Kahweol from Coffee Grounds on Serum Lipids and Serum Liver Enzymes in Humans, Am. J. Clin. Nutr. 61: 149–154, 1995.

Melnick et al., J. Invest. Dermoatol 92:231–234, 1989.

*Primary Examiner*—Neil S. Levy
*Attorney, Agent, or Firm*—Karen A. Lowney, Esq.

[57] ABSTRACT

The present invention relates to topical compositions useful in enhancing lipid synthesis in skin comprising an effective amount of cafestol, in combination with a pharmaceutically or cosmetically acceptable carrier. Such compositions are useful in treatment or prevention of dry skin and conditions in which the skin's lipid barrier is defective or damaged.

14 Claims, 6 Drawing Sheets

TOPICAL COMPOSITION AND METHOD FOR ENHANCING LIPID BARRIER SYNTHESIS

FIELD OF THE INVENTION

The present invention relates to topically applied compositions which increase lipid synthesis in skin. More specifically, the invention relates to compositions comprising cafestol as a lipid barrier enhancer.

BACKGROUND OF THE INVENTION

Skin is typically characterized as consisting of three distinct layers, namely the stratum corneum, the epidermis and the dermis. The stratum corneum, the outermost layer, is made up of keratinized cells, surrounded by intercellular space filled with lipids. The stratum corneum provides a substantial physical barrier to penetration of most substances to the lower layers of the skin. In addition to preventing transport of substances to the other skin layers, however, this barrier also aids in prevention of water loss from the skin. Both functions are primarily attributable to the presence of the lipids in the stratum corneum.

There are two sources of the skin surface lipids making up this important barrier: sebaceous glands and the epidermis. The lipids are a diverse group of compounds, comprising triglycerides, diglycerides, ceramides, free fatty acids, wax esters, cholesterol and cholesterol esters, and squalene. The quantity and composition of the skin surface lipids differ from place to place on the body, and may to some extent be related to the number of sebaceous glands in a given area of the skin. The condition of the skin surface lipids may also be affected by an essential fatty acid deficiency. Additionally, the lipid barrier is easily diminished by exposure to harsh detergents or soaps. It is apparent, then, that the quality of the skin lipid barrier can vary widely, depending on a number of different factors, and therefore, may not always be adequate to perform its protective function optimally.

As an attempt to compensate for what may be a less than adequate lipid barrier, cosmetic compositions frequently incorporate components which compensate for water loss. Examples of such materials are hygroscopic humectants, e.g., urea or propylene glycol; or emollients, e.g., oleyl alcohol or caprylic/capric triglycerides. Certain cosmetic components may be occlusive skin conditioners, which are used to provide an "artificial" barrier; such compounds are frequently lipids which remain on the skin surface, and include various hydrogenated oils, waxes and butters. Although many of these products provide an effective means of stemming water loss from the skin, they do have to be reapplied frequently to maintain the effect, and do not generally constitute a natural-occurring component of the stratum corneum, potentially giving rise to an unnatural, greasy feel to the skin. In addition, various pharmaceutical or cosmetic active agents are also frequently used to treat the symptoms of dry skin-associated conditions; however, in many cases, particularly with pharmaceutical agents, the treatments themselves may cause undesirable side effects in the individual being treated, while ultimately resulting in no actual repair of the lipid barrier.

The present invention now provides a useful substitute for the daily application of skin conditioning agents, or harsh topical active agents. It has now been discovered that it is possible to actually amplify the production of the skin's natural lipid barrier. Specifically, it has been found that cafestol, when applied topically to the skin, is capable of stimulating the production of one or more of the naturally occurring stratum corneum lipid components, as well as increasing the stratum corneum per se. There is thus provided a new type of cosmetic or pharmaceutical composition which functions by enhancing the skin's own functions, resulting in a more natural means of preventing dry skin and other undesirable results of a deficient lipid barrier.

SUMMARY OF THE INVENTION

The present invention relates to topical compositions comprising as an active component an effective amount of cafestol, or derivatives thereof, in combination with a cosmetically or pharmaceutically acceptable carrier. The invention also relates to a method for increasing lipid synthesis in the skin which comprises applying to the skin an effective amount of cafestol or a derivative thereof. As the lipid barrier is a key factor in maintaining the quality and moisture of skin, the topical application of cafestol or its derivatives is thus also useful in improving overall skin condition, and in the prevention or treatment of a variety of dry skin generally, and specific skin conditions in which the natural lipid barrier is compromised or absent.

DETAILED DESCRIPTION OF THE INVENTION

Cafestol is a diterpene which occurs naturally in, among other sources, coffee bean oil. Cafestol has the following chemical formula:

It is available commercially in esterified form as cafestol acetate. Diverse biological activities have been attributed to cafestol and related compounds. For example, coffee bean oil, which contains cafestol, has been said to be useful as a sun filter (U.S. Pat. No. 4,793,990). An extract of essential oils of coffee has been used, in combination with numerous other components, including cocoa butter and antioxidants, in toilet soap compositions; the components are said to synergistically interact to provide a "monomolecular film" on the skin (SU 1770352). Further, cafestol itself, in combination with another coffee bean oil component, kahweol, has been suggested as having a protective effect against carcinogens in animal subjects (Miller et al., Nutr. Cancer 15: 41–46, 1991; Huggett and Schilter, Colloq. Sci. Int. Cafe [C.R.] 16(1): 65–72, 1995. Cafestol and kahweol have also been linked to increasing serum lipid concentrations in individuals consuming significant quantities of unfiltered coffee (Urgert et al., Am. J. Clin. Nutr. 61: 149–154, 1995).

It has not heretofore been recognized, however, that cafestol alone, when applied directly to the skin, would have the significant biological activity of stimulating lipid production in the stratum corneum. It is therefore an unexpected observation that the application of small amounts of cafestol to living skin models results in a significant, dose-dependent increase in more than one major stratum corneum lipid. In addition, the amount of ceramide increases in a time-dependent manner with repeated applications of a uniform dosage over a period of days. Histological samples of the treated skin show that after treatment there is also a measurable increase in stratum corneum, suggesting that the treatment promotes differentiation of epidermal cells into stratum corneum; the increased presence of ceramides, which are differentiation-specific, is consistent with this scenario. Significantly, coffee bean oil, when used alone in the same treatment regimen, has no substantially no effect. In clinical studies, these results are also confirmed by an observation of an increase in ceramides in treated test subjects, and further by a showing of an increase in barrier strength in treated subjects.

In view of this activity, cafestol is a very useful component for cosmetic and/or topically delivered pharmaceutical compositions. As used in the present specification and claims, "effective amount" is intended to indicate an amount capable of increasing the production of at least one lipid barrier component by at least 1% when compared with untreated skin in the same location. Preferably, at least one lipid in increased by at least 5%. Alternately, the efficacy of cafestol is evaluated by its ability to strengthen the lipid barrier as indicated by measurement of transepidermal water loss. In the present context, an amount of cafestol is considered effective if it enhances lipid barrier strength by at least 5%, preferably at least 10%, after at least 5 days of treatment. In formulating such compositions, cafestol is incorporated in an amount of from about 0.001 to 50 mg/ml, preferably about 0.005 to 10.0 mg/ml, and more preferably about 0.1 to 1.0 mg/ml of composition. It will be understood that throughout the specification and claims, where the term "cafestol" is used, this term also encompasses, in addition to cafestol per se, any and all safe and effective derivatives, analogs, or precursors of cafestol, e.g., esters, such as cafestol acetate, cafestol palmitate and cafestol diacetate; cafestol toluenesulfonate; and 16, 17 anhydrocafestol, or any mixtures thereof. Preferably, the cafestol or derivative thereof is substantially pure, i.e., at least 70% pure, preferably at least 80% pure and more preferably at least 90% pure.

For topical application, cafestol can be formulated with a variety of cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co. Easton, Pa., 1990. The carrier may be in any form appropriate to the mode of delivery, for example, solutions, colloidal dispersions, emulsions (oil-in-water or water-in-oil), suspensions, creams, lotions, gels, foams, mousses, sprays and the like.

The formulation, in addition to the carrier and cafestol, also can comprise other components which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like.

The therapeutic/cosmetic uses of the present compositions are numerous, namely treatment or prevention of any condition in which the skin's natural lipid barrier is at risk, deficient or damaged. For example, the cafestol-containing compositions can be used in prevention or treatment of dry skin conditions generally, or specific dry skin conditions, such as result from regular exposure to detergents, soaps and hot water; seasonal exposure to harsh weather conditions, e.g., cold, wind and/or sun; occupational exposure to harsh chemicals or other drying or damaging agents; or pathological conditions such as eczematous dermatides, psoriasis, ichthyoses, xerosis and the like. It is also well-known that dry skin is commonly associated with aging (both intrinsic and photoaging), and the cafestol compositions can be used in prevention of further damage to aging skin, or treatment and/or reversal of already present damage. The compositions can also be used in the treatment of a defective skin barrier, such as occurs on the soles of the feet, and palms of the hands, where the stratum corneum is very thick, but the lipid barrier is poor. In addition, defective skin barriers frequently occur in association with burns, wounds, blisters, stasis ulcers and bedsores; such injuries can be expected to benefit from application of the cafestol compositions. The compositions may also be useful in enhancement of percutaneous drug delivery.

As will be apparent from the foregoing list of pertinent applications for the present compositions, they may also be beneficially combined with other active agents which are used for skin treatment (both cosmetic and pharmaceutical), or which are routinely applied topically. Examples of such active agents which may be usefully combined with cafestol include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, or hormones. More specific examples of useful active agents include retinoids, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinoic acid, 13-cis retinoic acid, hydrocortisone, hydrocortisone 21-acetate, hydrocortisone 17-valerate, hydrocortisone 17-butyrate, betamethasone valerate, betamethasone diproprionate, DHEA and derivatives thereof, triamcinolone acetonide, fluocinonide, clobetasol, proprionate, benzoyl peroxide, crotamiton, propranolol, promethazine, vitamin A palmitate, vitamin E acetate and mixtures thereof. The amount of active agent to be used in any given formulation is readily determined in accordance with its usual dosage.

The method and frequency of application of the compositions will vary depending upon the form of the composition and nature of the condition to be treated or prevented. As to method for application, the composition will generally be applied in the same manner as one would apply other compositions of the same type and form, e.g., as a cream or lotion to be applied for moisturizing the skin. As to frequency, for treatment of existing dry skin conditions or other conditions associated with a defective, damaged, or absent barrier, the composition can be applied, for example, on an as-needed basis until the condition is improved, or whenever exposure to causative exogenous conditions is frequent. The compositions can also be applied daily to prevent the occurrence of dry skin. When used in combination with other active agents, as outlined above, the application frequency will be determined according to the usual pattern for topical application of the other active.

The invention will be further understood by reference to the following non-limiting examples.

EXAMPLES

I. LIVING SKIN MODELS—MATERIALS AND METHODS

A. Determination of cafestol activity. Living skin models (#1301) are obtained from Advanced Tissue Sciences and treated with cafestol acetate (Sigma)by addition of a stock solution prepared in cell culture medium in a dose-dependent manner from 0.01 mg/ml to 1.0 mg/ml, or in a time-dependent manner at 0.5 mg/ml for up to 7 days. All experiments are conducted with untreated controls. At each dose or time point, the skin models are homogenized and the lipids extracted with chloroform/methanol (2:1), taken to dryness, and resuspended in chloroform. Samples are chromatographed on HPTLC and their lipid composition visualized by degradative charring (Melnick et al., J. Invest. Dermatol 92:231–234, 1989)

B. Comparison of cafestol activity with coffee bean oil activity. To compare the lipid enhancing activity of cafestol with that of coffee bean oil, living skin models are treated over a period of five days with increasing amounts of cafestol acetate in a range form 0.01 mg/ml to 1.0 mg/ml. A parallel set of living skin squares is also tested with a sample of coffee bean oil (Robeco). At the end of the incubation period, each skin square is homogenized and its lipids extracted in chloroform/methanol (2:1). This is followed by TLC analysis. Ceramides are identified by degradative charring and comparison to ceramide standards. Densitometric analysis of the TLC plate is carried out with an Optimas Bioscan.

C. Histology. To determine the histological effect of cafestol application to living skin, skin squares are treated as described above; at the end of the incubation period, samples are fixed, sectioned and stained with hematoxylin/eosin.

II. LIVING SKIN MODELS—RESULTS

Figure 1:
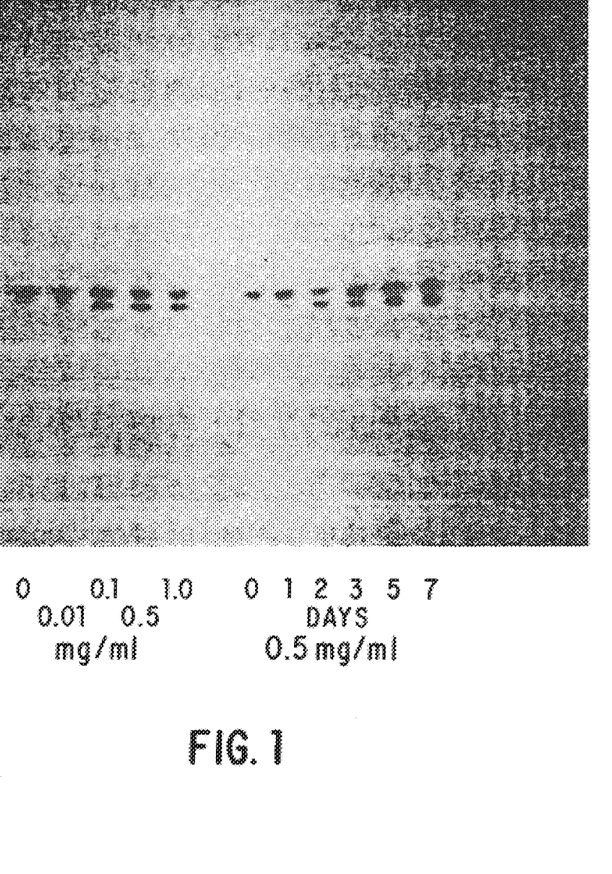
FIG. 1 is photograph of a TLC plate showing the results of dose-variable (left) and time-variable (right) application of cafestol acetate to living skin models. Each shows an increase in ceramide production with increasing dosage and time.

Two dose-dependent experiments are carried out on two separate batches of living skin models. The HPTLC results from both experiments clearly show a selective increase in ceramides as a function of dose. Also, the time-dependent experiment clearly shows the presence of ceramides after only one day of application, reaching maximum concentrations after three days (FIG. 1).

Figure 2:
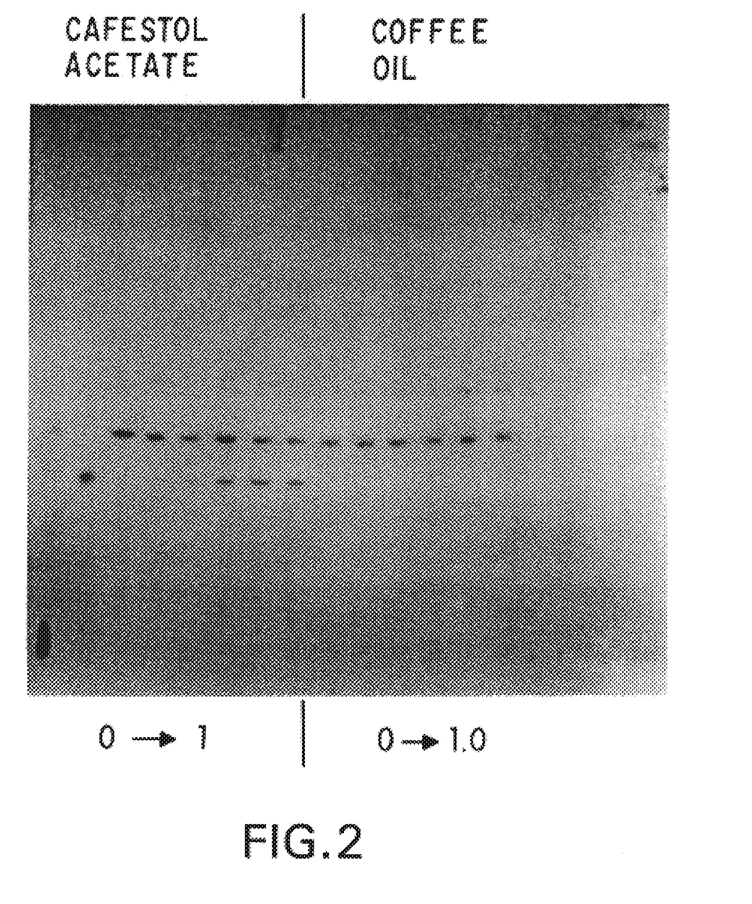
FIG. 2 is a photograph of a TLC plate showing the results of a comparison between application of cafestol acetate and coffee bean oil to living skin models, with respect to dose-dependent increase in ceramide production.
Figure 3:
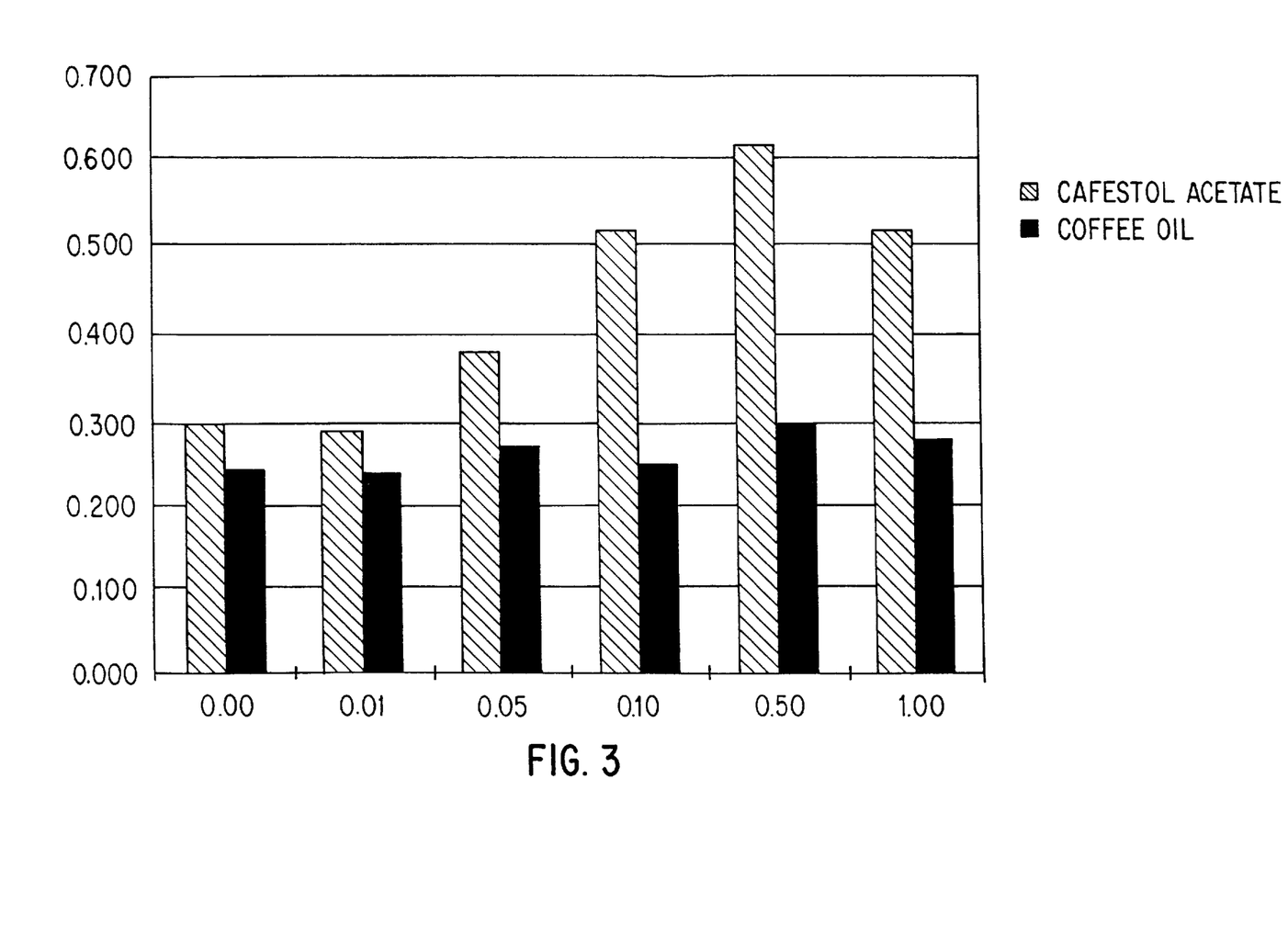
FIG. 3 is a graphic representation of densitometric analysis of the TLC plate shown in FIG. 2, showing the effect of each treatment on ceramide content of skin relative to dosage.

The comparative testing with coffee bean oil confirm the original results, showing a dose-dependent increase in ceramide production in the cafestol-treated skin (FIG. 2) The densitometric scan of the TLC plate reveal a pattern consistent with this finding. However, coffee bean oil, which contains cafestol acetate, appears to increase ceramides only very slightly (FIG. 3). Histological analysis of the treated samples shows a clear increase in stratum corneum, indicating that the treatment actually induces stratum corneum differentiation, an assumption further borne out by the increase in ceramides, which are known to be differentiation-specific.

III. CLINICAL STUDIES ON HUMAN SKIN— MATERIALS AND METHODS

A. Determination of cafestol activity on lipid production. An initial test on a single individual indicates that ceramide I is elevated when cafestol is applied directly to skin over the course of three days. A short clinical study, consisting of five subjects, is then carried out under the same conditions in order to test the ability of cafestol acetate to raise ceramide levels.

At zero time, ethanol washes are performed in order to remove stratum corneum lipids from both arms. Cafestol acetate, prepared in ethanol at a concentration of 1 mg/ml, is applied twice a day with a pump spray to the right volar forearm. As a control, ethanol is applied at the corresponding site at the left arm. On day three, stratum corneum lipids are again removed and both zero time and day three lipids from both arms are evaluated by thin layer chromatography as described above.

B. Effect of cafestol on skin barrier function. Ten healthy female subjects, between the ages of 25–45. with normal skin on their forearms are tested in this study. The subjects do not use any treatment or cosmetic products on the day of testing. They acclimate in the environmental room at 40% relative humidity and 70° F. for 20 minutes before their baseline measurements are recorded. They are then randomly assigned to one of two treatment groups.

Group I (n=5) receives treatment containing cafestol at 0.1% to use on one arm and a placebo to use on the other arm. Group II (n+5) uses a treatment containing 0.2% cafestol palmitate on one arm and a treatment containing 0.1% cafestol acetate on the other arm. The subjects self-administer the treatment twice a day on the lower part of their volar forearms except on the day of testing.

A five cm by two cm are is marked using a template on the lower inner forearm and initial water evaporation measurements are taken in three separate spots approximately 1 cm apart in a row. Five cm of the cello-tape is placed on the skin in the outlined area, starting from the top and after one firm stroke in each direction is removed by gently pulling in a downward direction parallel to the skin. The procedure is repeated and water evaporation is measured after every five to ten strips until the barrier is broken, as indicated by a minimum water evaporation of 18 g/sq m hr on one of the three spots. The subjects' transepidermal water loss (TEWL) is monitored on the challenged sites after 1, 2 and 3 days in order to measure the ability of the skin to repair itself. After 5 and 10 days of product treatment, the above procedure is repeated under the same test conditions on an adjacent new site.

TEWL is measured with the Servo Med Evaporimeter, fitted with a chimney and gauze. The subjects are in a relaxed inclined position, and are not allowed to converse or get excited. TEWL is recorded automatically using the Dia-Stron computer program set at a 30 second data acquisition time and a 15 second plateau.

IV. CLINICAL STUDIES ON HUMAN SKIN—RESULTS

A. Measure of ceramide levels on human skin. Thin layer chromatography shows that arms which receive cafestol treatment have increased levels of ceramide I in four of the five subjects, although intensity varies among subjects. In addition, the subject which does not show an increase in ceramide I shows an increase in ceramide IV.

B. Barrier strength measurements. Barrier strength is evaluated by challenging the skin with tape stripping and measuring the water evaporation (WE). To describe the experimental data, curve fitting Linear Regression Analysis based on least-square method is performed on each individual's data and the number of tape strippings required to reach a WE of 18 g/sq m/hr is recorded for each visit. The number of tape strippings required to perturb the barrier is a measure of its strength.

Figure 4:
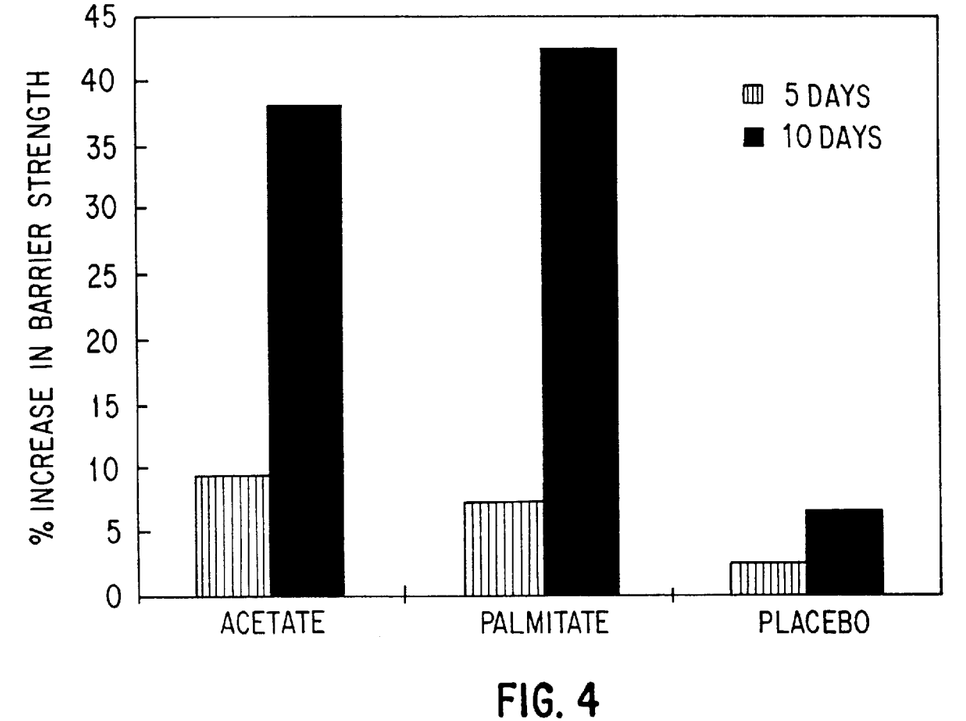
FIG. 4 is a graphic representation of the effect of cafestol acetate and cafestol palmitate on barrier strength measured via tape stripping and TEWL.
Figure 5:
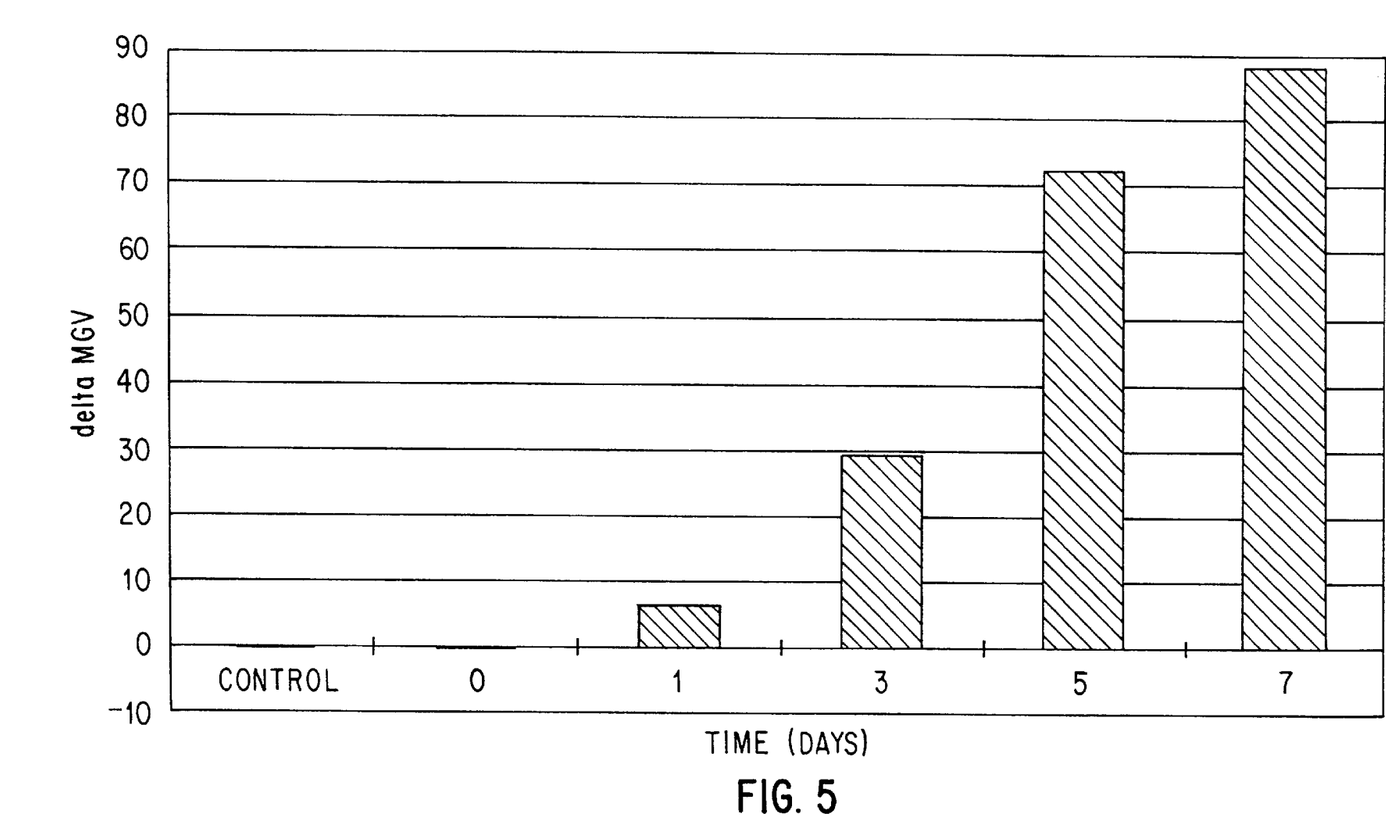
FIG. 5 is a graphic representation of the effect of cafestol on ceramide production in skin over time.
Figure 6:
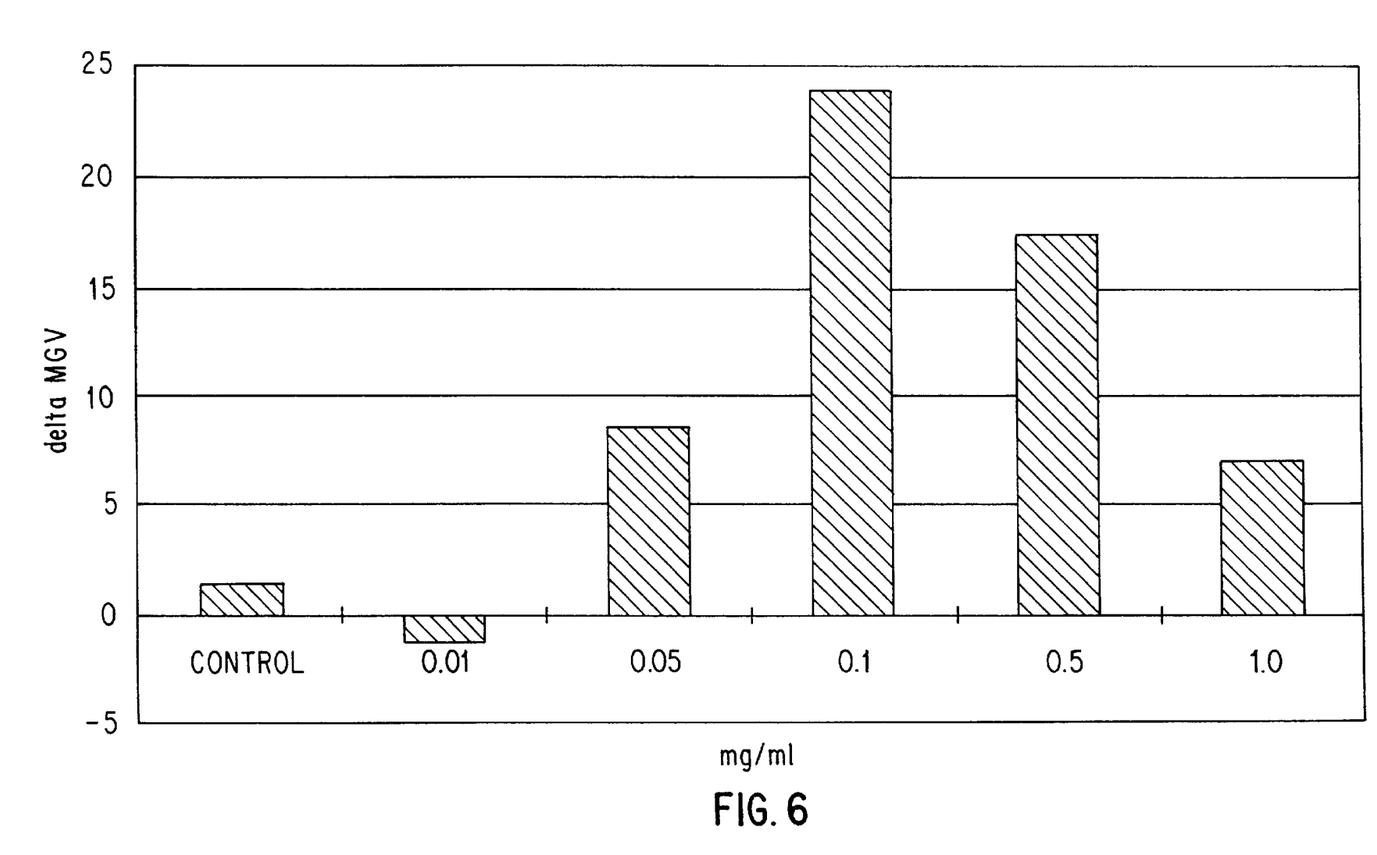
FIG. 6 is a graphic representation of a dose-dependent effect of cafestol on ceramide production in skin

Based on this assessment, the group using the cafestol acetate showed a 10% and a 38% increase in barrier strength after 5 and 10 days of treatment, the cafestol palmitate shows an 8% and a 43% increase and the placebo-treated group shows a 3% and 7% increase. FIG. 4 summarizes these results.

The rate of repair is monitored on the stripped sites for three days. The percent increase in TEWL and its recovery are calculated at baseline, and after 5 and 10 days of treatment. These results do not show any change in the rate of barrier repair with treatment.

What we claim is:

1. A topical composition comprising as an active component an amount of a substantially pure cafestol compound effective in increasing strength of the lipid barrier, as measurable by a reduction in transepidermal water loss, in combination with a cosmetically or pharmaceutically acceptable carrier.

2. The composition of claim 1 in which the cafestol is in the form of a cafestol ester.

3. The composition of claim 1 in which the cafestol ester is cafestol acetate or cafestol palmitate.

4. The composition of claim 1 in which the effective amount of cafestol is from about 0.001 to about 50 mg/ml.

5. The composition of claim 1 in which the effective amount of cafestol is from about 0.005 to about 10.0 mg/ml.

6. The composition of claim 1 in which the effective amount of cafestol is from about 0.1 to about 1.0 mg/ml.

7. The composition of claim 1 which further comprises an additional cosmetic and/or pharmaceutical topically active agent.

8. A method for increasing ceramide synthesis in the skin which comprises applying to the skin, for a time sufficient to increase ceramide synthesis, an amount of a substantially pure cafestol compound effective to increase the production of ceramide by at least 1%.

9. A method for strengthening the lipid barrier in skin which comprises applying, for a time sufficient to strengthen the barrier, the composition of claim 1.

10. The method of claim 8 in which the lipid is Ceramide I or Ceramide IV.

11. The method of claim 8 in which the cafestol is in the form of cafestol acetate or cafestol palmitate.

12. A method for improving skin condition which comprises applying to the skin, for a time sufficient to increase strength of the lipid barrier, a topical composition comprising as an active component an amount of a substantially pure cafestol compound effective in increasing strength of the lipid barrier, as measurable by a reduction in transepidermal water loss, in combination with a cosmetically or pharmaceutically acceptable carrier.

13. A method for treatment or prevention of dry skin conditions which comprises applying to the skin, for a time sufficient to increase strength of the lipid barrier, a topical composition comprising as an active component an amount of a substantially pure cafestol compound effective in increasing strength of the lipid barrier, as measurable by a reduction in transepidermal water loss, in combination with a cosmetically or pharmaceutically acceptable carrier.

14. A method for treating skin conditions associated with a defective or diminished lipid barrier which comprises applying to the skin, for a time sufficient to increase the strength of the lipid barrier, a topical composition comprising as an active component an amount of a substantially pure cafestol compound effective in increasing strength of the lipid barrier, as measurable by a reduction in transepidermal water loss, in combination with a cosmetically or pharmaceutically acceptable carrier.

* * * * *